United States Patent
Dissel

(10) Patent No.: US 12,226,264 B2
(45) Date of Patent: Feb. 18, 2025

(54) MEDICAL LIGHTING DEVICE, SYSTEM FOR FLUORESCENCE IMAGE GUIDED SURGERY AND METHOD TO MANUFACTURE A MEDICAL LIGHTING DEVICE

(71) Applicant: OLYMPUS Winter & Ibe GmbH, Hamburg (DE)

(72) Inventor: Matthias Dissel, Hamburg (JP)

(73) Assignee: Olympus Winter & Ibe GmbH, Hamburg (DE)

( * ) Notice: Subject to any disclaimer, the term of this patent is extended or adjusted under 35 U.S.C. 154(b) by 316 days.

(21) Appl. No.: 18/075,689

(22) Filed: Dec. 6, 2022

(65) Prior Publication Data

US 2023/0181281 A1 Jun. 15, 2023

Related U.S. Application Data

(60) Provisional application No. 63/288,207, filed on Dec. 10, 2021.

(51) Int. Cl.
*A61B 90/30* (2016.01)
*A61B 5/00* (2006.01)

(52) U.S. Cl.
CPC ............ *A61B 90/30* (2016.02); *A61B 5/0071* (2013.01); *A61B 2090/306* (2016.02); *F21V 2200/13* (2015.01)

(58) Field of Classification Search
CPC .............. A61B 90/30; A61B 2090/304; A61B 2090/306; A61B 2090/308; A61B 2090/309; A61B 5/0071; F21V 2200/10; F21V 2200/13
See application file for complete search history.

(56) References Cited

U.S. PATENT DOCUMENTS

| | | | |
|---|---|---|---|
| 6,697,666 B1* | 2/2004 | Richards-Kortum | ........................ A61B 5/0071 600/478 |
| 2014/0357948 A1 | 12/2014 | Kikuchi et al. | |
| 2016/0058383 A1 | 3/2016 | Hellstrom et al. | |
| 2019/0008376 A1* | 1/2019 | Wortelboer | .......... A61B 5/6852 |

FOREIGN PATENT DOCUMENTS

| | | |
|---|---|---|
| DE | 10 2019 218 065 A1 | 5/2021 |
| WO | 2002/096478 A2 | 12/2002 |
| WO | 2012/170401 A2 | 12/2012 |
| WO | 2015183074 A1 | 12/2015 |
| WO | 2017/104047 A1 | 6/2017 |

* cited by examiner

*Primary Examiner* — Sean P Gramling
(74) *Attorney, Agent, or Firm* — Scully, Scott, Murphy & Presser, P.C.

(57) ABSTRACT

A medical lighting device, a system for fluorescence image guided surgery and a method to manufacture a medical lighting device are provided. The medical lighting device includes a device body and light guiding optics. The light guiding optics comprise optical fibers and a first ring-shaped mirror encircling the device body. A segment of each optical fiber passes through the first ring-shaped mirror while being guided towards the distal end. After passing through the first ring-shaped mirror, a light guiding element redirects one or more of excitation light and white light ack towards the first ring-shaped mirror. The first ring-shaped mirror reflects the one or more of the emitted excitation light and the white light towards the area to be illuminated by the one or more of the excitation light and the white light.

21 Claims, 4 Drawing Sheets

MEDICAL LIGHTING DEVICE, SYSTEM FOR FLUORESCENCE IMAGE GUIDED SURGERY AND METHOD TO MANUFACTURE A MEDICAL LIGHTING DEVICE

CROSS-REFERENCE TO RELATED APPLICATION

The present application is based upon and claims the benefit of priority from U.S. Provisional Patent Application No. 63/288,207 filed on Dec. 10, 2021, the entire contents of which is incorporated herein by reference.

BACKGROUND

Field

The present disclosure relates to a medical lighting device for guiding excitation light during fluorescence image guided surgery towards a surgical area. The present disclosure further relates to a system for fluorescence image guided surgery and a method to manufacture a medical lighting device.

Prior Art

Fluorescence image guided surgery is a technique utilized to highlight certain areas or masses during surgery to aid in navigation. In this technique, fluorescence dyes and/or fluorescent proteins are used to mark certain molecules in the surgical area. When radiated with excitation light of the appropriate wavelength, the so marked molecules will emit a fluorescent light. The fluorescent light can be de-tected either directly by the surgeon or by a camera system, if the wavelength of the fluorescent light is outside the visible spectrum.

WO 2015/183074 A1 shows a two dimensional imaging system, which comprises a measurement device usable for fluorescence image guided surgery. A number of LED lights or optical fibers are arranged in a ring-shaped mounting surrounding a tubular device body. Through a number of lenses, the LEDs project their light forward towards the surgical area, where the light excitates the marked molecules, which in turn emit the fluorescent light. A lens unit arranged inside the tubular device body captures the fluorescent light and sends it to an imaging system. The imaging system comprises sampling units, which collect data from the fluorescent light and send it to a processing unit, which converts the data into an image.

However, the structure of the ring-shaped mounting with its LEDs or optical fibers arranged in individual openings is complex and difficult to manufacture. In addition, it is not possible to steam-sterilize the device with an autoclave.

SUMMARY

It is an object to provide a medical lighting device for guiding excitation light, a system for fluorescence image guided surgery and a method to manufacture a medical lighting device, that are easy to manufacture and allow a steam-sterilization of the device.

Such object can be solved by a medical lighting device for guiding excitation light and/or white light during fluorescence image guided surgery towards a surgical area, the medical lighting device comprising a device body and light guiding optics, wherein the device body extends longitudinally in the direction of a central axis from a proximal end to a distal end of the device body, towards an area to be illuminated by the excitation light and/or white light, wherein the light guiding optics comprise optical fibers and a first ring-shaped mirror encircling the device body in a circumferential direction of the device body, wherein the optical fibers each extend from a first fiber end, configured to receive the excitation light, to a second fiber end, configured to emit the excitation light and/or white light, wherein a segment of each optical fiber passes through the first ring-shaped mirror while being guided in a forward direction towards the distal end, wherein the ends of the segments are the second fiber ends, wherein, after passing through the first ring-shaped mirror, at least one light guiding element redirects the excitation light and/or white light from the forward direction to a changed direction back towards the first ring-shaped mirror, wherein a reflecting surface of the first ring-shaped mirror is arranged in a path of the emitted excitation light and/or white light, wherein the first ring-shaped mirror is configured and arranged to reflect the emitted excitation light and/or white light from the changed direction towards the area to be illuminated by the excitation light and/or white light.

By redirecting the excitation light from the forward direction to a changed direction and then reflecting the excitation light towards the area to be illuminated, it is not necessary to provide a complex ring-shaped mounting at the distal end of the medical lighting device to receive the second fiber ends. Instead, the excitation light is redirected by the light guiding element and afterwards reflected to the area by the first ring-shaped mirror. This setup is easier to manufacture than the ring-shaped mounting and can be steam-sterilized, as there is no mounting with individual openings necessary through which the optical fibers are guided.

In addition, or instead of guiding excitation light, the medical lighting device may also be applied to guide white light to illuminate the area during the surgery. The excitation light and the white light can be guided together through the same optical fibers, which means that a mixture of excitation light and white light are guided in the optical fibers. Within the context of this specification "white light" is considered to be visible light, i.e., light visible to the human eye, having a spectrum comparable to a white light source like for example a light bulb, a discharge lamp, a white LED or even sunlight.

The distal end of the device body is the part of the device body closest to the area to be illuminated. According to an embodiment, the forward direction can be parallel to the central axis of the medical lighting device. In this embodiment, the forward directions of all optical fibers are identical axial directions. According to a different embodiment, the forward directions of one or more of the optical fibers are different from each other. However, in both embodiments the forward directions run towards a distal end of the device body. The central axis is for example a direction, in which the medical lighting device emits the excitation light towards the area to be illuminated. The area to be illuminated can be located in front of the device body, in a location situated along the central axis.

The excitation light according to an embodiment may be any suitable electromagnetic radiation suitable for fluorescence image guided surgery and is not restricted to light with a wavelength in the visible spectrum. The excitation light and/or white light can be created by a light source. The excitation light and/or white light can be guided through the optical fibers, which travel at least in part along the forward direction. The redirection of the excitation light and/or white light from the forward direction to the changed direction may happen while the excitation light and/or white light is still guided within the optical fibers or after the excitation light and/or white light has been emitted from the second fiber ends. The light guiding element can redirect the excitation light and/or white light outwards, away from the device body. After the excitation light and/or white light is redirected, the excitation light and/or white light is reflected by the reflecting surface of the first ring-shaped mirror towards the area to be illuminated by the excitation light and/or white light. During the fluorescence image guided surgery, the area to be illuminated by the excitation light and/or white light is the surgical area.

According to an embodiment, the paths of the excitation light inside the segments of the different optical fibers can be parallel to each other, all running along the same forward direction, such as along a cylindrical surface. According to a different embodiment, the paths of the excitation light inside the segments of the different optical fibers are not parallel to each other, but can be symmetrical to the central axis. In other words, in this embodiment the forward directions of the optical fibers are not identical.

For each optical fiber, the excitation light and/or white light can be redirected by the at least one light guiding element from the forward direction to a different changed direction. The different changed directions can all include the same angle with the respective forward direction. For example, the paths of the excitation light and/or white light in the different changed directions form a part of a cone surface.

The segments of multiple optical fibers can be arranged in a ring like fashion, wherein the segments can surround the device body in a circumferential direction. The optical fibers can approach the device body only from one side, without surrounding it fully. Only at an axial position, where the segments start, the optical fibers start encircling the device body entirely. The optical fibers can run along a surface of the device body, such as an outer surface of the device body.

An angle between the forward direction and the changed direction can be between 90° to 175°, such as 120° to 170 or 140° to 160°.

The angle may be for example 150° or any other angle suitable to redirect the excitation light back towards the reflective surface of the first ring-shaped mirror, so that the excitation light can reach the area to be illuminated. The angle is measured between the direction in which the excitation light and/or white light travels along the forward direction and the changed direction, in which the excitation light and/or white light travels after it has been redirected.

According to an embodiment, at least one of the light guiding elements can be an end segment of at least one of the optical fibers, wherein the end segment is bent from the forward direction to the changed direction, so that the second fiber end is positioned to emit the excitation light and/or white light in the changed direction towards the reflecting surface of the first ring-shaped mirror.

According to this embodiment, the excitation light and/or white light can be redirected while still being guided within the optical fibers. Advantageously, this allows for an easily manufacturable medical lighting device and does not cause problems during sterilization. The end segment of the at least one optical fiber can be located at the distal end of the device body. The end segment can be bent out-wardly away from the device body. End segments of multiple optical fibers can be bent in a ring like fashion to the outside. The bending of the end segments can be symmetrical to the central axis of the device body. The end segment can bend in a way as to observe a minimal bending radius of the optical fiber. In this way, the optical fibers stay undamaged during manufacture of the medical lighting device.

The distal end of the device body can comprise a sleeve, wherein the sleeve can comprise a curvature, wherein the end segment of the at least one optical fiber is bent by the curvature.

The sleeve with its curvature offers a simple and reliable way to bend the end segments of the optical fibers while observing the minimal bending radius. The sleeve can be fixed, such as screwed or glued, to the device body or is a part of the device body. The sleeve can extend along a circumferential direction of the device body. The curvature itself can extend in a plain mounted by the forward direction and a radial direction of the device body.

According to another embodiment, at least one of the light guiding elements can be a second ring-shaped mirror, wherein at least one of the second fiber ends can be arranged to emit the excitation light and/or white light in the forward direction towards the second ring-shaped mirror, wherein the second ring-shaped mirror can be configured and arranged to reflect the excitation light and/or white light in the changed direction towards the reflecting surface of the first ring-shaped mirror.

According to this embodiment, the excitation light and/or white light can be redirected after being emitted by the second fiber ends of the optical fibers. The second ring-shaped mirror can offer another easily manufacturable solution to redirect the excitation light and/or white light towards the first ring-shaped mirror. The second ring-shaped mirror can be arranged at the distal end of the device body.

The device body can comprise an inner device body and an outer device body, wherein the outer device body can surround the inner device body in the circumferential direction, wherein the first ring-shaped mirror can surround the outer device body in the circumferential direction, wherein the segments can pass through the first ring-shaped mirror by passing through a gap between an inner surface of the outer device body and an outer surface of the inner device body.

By splitting the device body into the inner device body and the outer device body, the assembly of the medical lighting device can be simplified. The inner device body has the form of a hollow cylinder. The optical fibers can be guided between the first ring-shaped mirror and/or the outer device body on one side and the inner device body on the other side. The sleeve can be fixed to the inner device body or is a part of the inner device body. The inner device body can be a lens tube comprising a lens unit. The lens unit can be configured to capture fluorescent light.

The outer device body can be fixed, such as screwed and/or glued, on the inner device body and/or the optical fibers to hold the optical fibers in place.

This setup is especially advantageous if the end segments are bent to redirect the excitation light and/or white light. The segments of the optical fibers can be placed on an outer surface of the inner device body and the end segments can be arranged in the curvature. Afterwards, the outer device body can be fixed on top of the optical fibers and/or the inner device body, so that the segments of the optical fibers are held in place between the inner device body and the outer device body and the end segments are held in the curvature.

The first ring-shaped mirror can be a concave mirror, wherein the second ring-shaped mirror can be a convex mirror.

A concave mirror can offer an easy solution to reflect the redirected excitation light and/or white light and focus it in the area to be illuminated. The at least one light guiding element directs the excitation light and/or white light outwardly, away from the device body and the central axis of the device body, wherein the concave mirror refocuses the excitation light and/or white light emitted by the optical fibers towards a small area. By configuring the second ring-shaped mirror as a convex mirror, the redirection of the emitted excitation light and/or white light can be directed away from the device body.

The first ring-shaped mirror can be shaped as a parabolic or spherical reflector with a circular recess in its middle, wherein the device body can be arranged in the circular recess.

In other words, the central part of the mirror can be cut out, giving the mirror its ring-shaped form. The circular recess allows the device body to be arranged inside the first ring-shaped mirror. The first ring-shaped mirror may be a separate component to the device body or the first ring-shaped mirror may be a single piece component together with the device body. To pass through the first ring-shaped mirror, the segments may pass through the circular recess or may pass through a separate gap in the first ring-shaped mirror. The second ring-shaped mirror can be shaped as a parabolic or spherical reflector with a circular recess in its middle.

The first ring-shaped mirror can be movable parallel to the central axis of the device body in relation to the light guiding element, such as in relation to the inner device body.

By moving the first ring-shaped mirror parallel to the central axis, a focus of the medical lighting device may be changed. Depending on the distance of the surgical area to the medical imaging device, an axial position of the first ring-shaped mirror may be adjusted to ensure an appropriate illumination of the surgical area with the excitation light and/or white light.

According to an embodiment, the device body can have a tubular form with an opening, the opening can extend along the central axis, wherein the segments of the optical fibers can run outside a surface area of the device body.

The opening can be configured to hold a lens unit to capture the fluorescent light. The medical lighting unit can comprise the lens unit arranged inside the device body.

Such object can be further solved by a system for fluorescence image guided surgery, comprising a medical lighting device according to any of the previously discussed embodiments, a light source to provide excitation light and/or white light for the medical lighting device, a lens unit to capture fluorescence light from the surgical area and an image sensor arranged to receive the fluorescent light from the lens unit.

The same or similar advantages apply to the system for fluorescence image guided surgery as were previously mentioned with respect to the medical lighting device.

The system for fluorescence image guided surgery employs the medical lighting device to illuminate a surgical area with the excitation light. The resulting fluorescent light is captured by the lens unit, which sends the fluorescent light to the image sensor. The image sensor can transform the fluorescent light into data, the data being utilized to highlight the marked region in a medical image. For example, the image sensor can be a CCD to transform the fluorescent light into a signal. The lens unit can be configured and arranged to guide the fluorescent light from the surgical area to the image sensor.

Such object can be further solved by a method to manufacture a medical lighting device according to any of the previously mentioned embodiments, wherein the segments of the optical fibers are arranged at different circumferential positions of the device body, each segment extending along the forward direction.

The same or similar advantages apply to the method to manufacture a medical lighting device as were previously mentioned with respect to the medical lighting device or the system for fluorescence image guided surgery.

By arranging the segments at different circumferential positions, the segments can surround the surface of the device body.

The optical fibers can be glued together and/or smoothed and/or polished after being arranged at different circumferential positions.

By treating the optical fibers in this way, a clean surface is provided that allows for an easy assembly of the medical lighting device. The optical fibers can be glued together to form a band of optical fibers. The band of optical fibers can surround a surface of the device body.

The segments of the optical fibers can be placed on the outer surface of the inner device body, wherein the segments can be fixed in this position by placing and fixing the outer device body on the inner device body, thereby enclosing the segments in the gap between the inner device body and the outer device body.

By enclosing the segments in the gap between the inner device body and the outer device body, the segments can be securely held in place.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on exemplary embodiments, wherein reference is made expressly to the drawings with regard to the disclosure of all details that are not ex-plained in greater detail in the text. The drawings show in.

In the drawings, the same or similar types of elements or respectively corresponding parts are provided with the same reference numbers in order to pre-vent the item from needing to be reintroduced.

DETAILED DESCRIPTION

Figure 1:
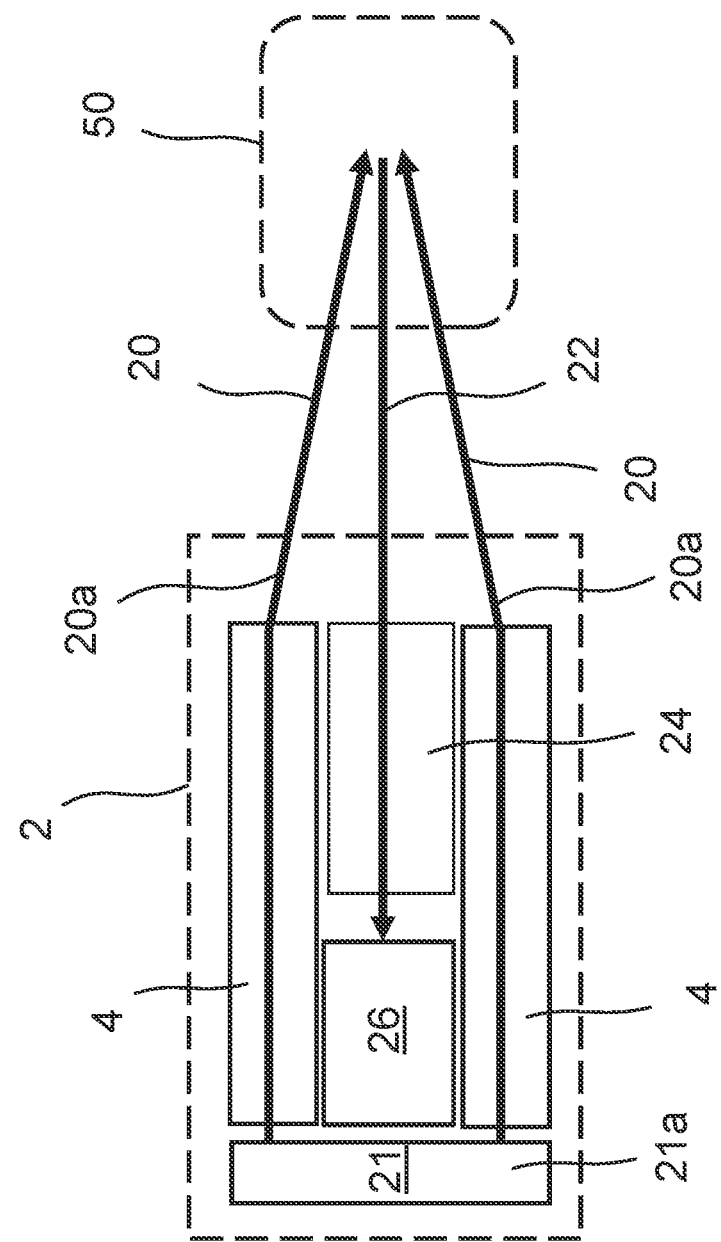
FIG. 1 illustrates a schematic simplified representation of a system for fluorescence image guided surgery.

FIG. 1 shows a schematic representation of an exemplary embodiment of a system 2 for fluorescence image guided surgery. The system 2 comprises a light source 21 which emits excitation light 20. The excitation light 20 may have any wavelength suitable for fluorescent image guided surgery and is not limited to the visible spectrum. A medical lighting device 4 guides the excitation light 20 and focusses it on an area 50 to be illuminated, for example a surgical area. In FIG. 1, the medical lighting device 4 is shown in two separate parts, indicating that it has a ring-like shape or a tubular shape, surrounding a lens unit 24. However, the medical lighting device 4 may have any other form suitable to illuminate the area 50. The area 50 contains matter marked with fluorescent markers. If this matter is excited with by excitation light 20, it emits fluorescent light 22. This fluorescent light 22 is captured by the lens unit 24 having one or more optical lenses (shown schematically by box 24), which guides it to an image sensor 26. The image sensor 26 comprises for example a CCD, which transforms the fluorescent light into data, which is used to highlight the marked matter in an image of the area 50. In this way, a surgeon can easily identify the marked matter in the image, allowing for a simplified navigation during surgery. Instead, or in addition to a light source 21 for emitting excitation light 20, the system may comprise a light source 21a configured to emit white light 20a. According to a different embodiment, the light source 21 may be configured to emit both the excitation light 20 and the white light 20a.

Figure 2:
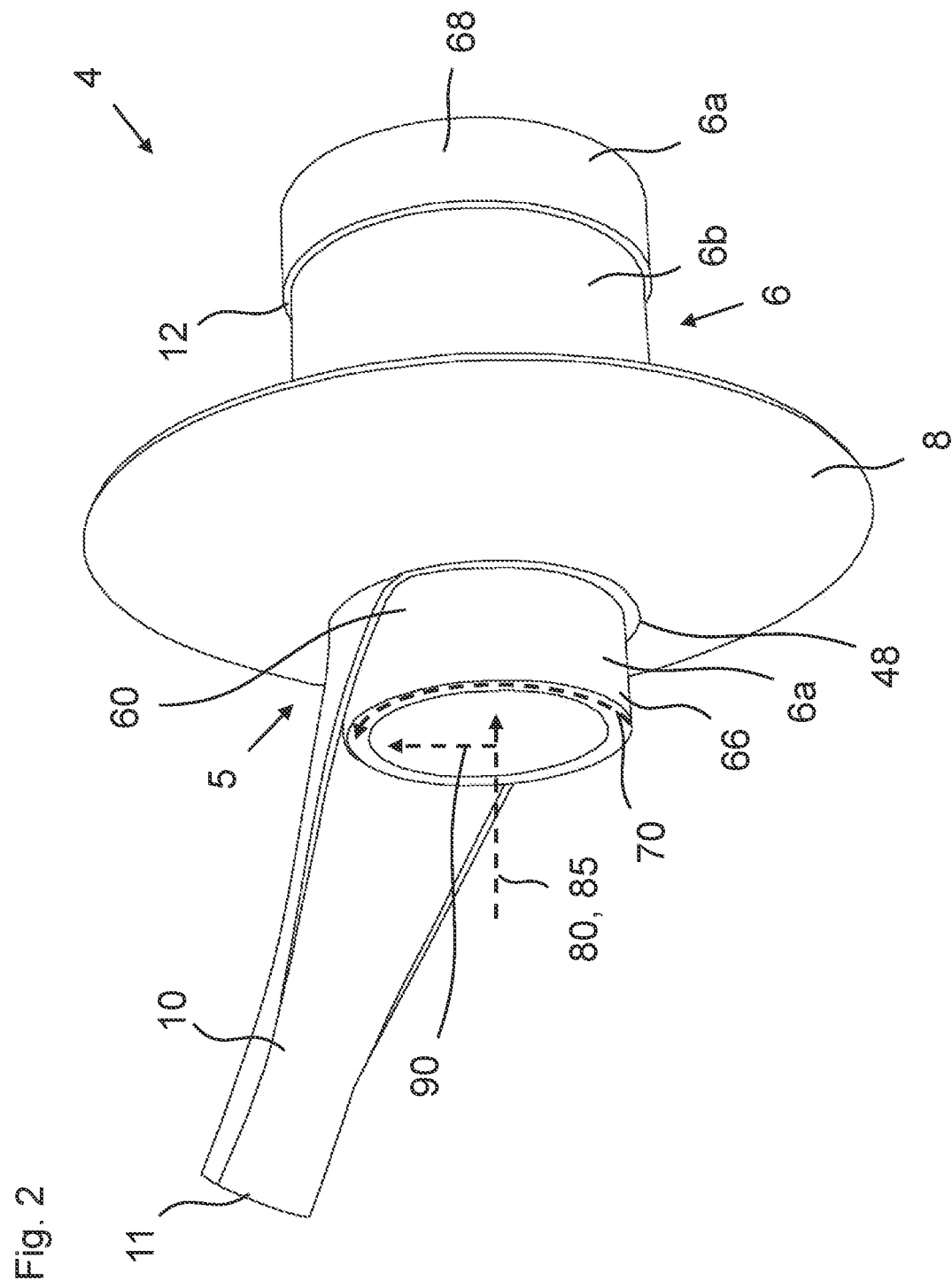
FIG. 2 illustrates a schematic perspective representation of a medical lighting device with a ring-shaped mirror.

FIG. 2 shows a schematic representation of an exemplary embodiment of a medical lighting device 4. The medical lighting device 4 comprises a tubular device body 6 and light guiding optics 5. The light guiding optics 5 comprise optical fibers 10 and a first ring-shaped mirror 8. In the embodiment shown in FIG. 2, the optical fibers 10 are glued together, polished and smoothed to create a band of optical fibers 10. Starting from a first fiber end 11, configured to receive the excitation light 20, the band of optical fibers 10 approaches the device body 6 from a single side. Starting approximately at a proximal end 66 of the device body 6, the optical fibers 10 start to envelope a surface area of the device body 6 completely.

The device body 6 comprises in this embodiment an inner device body 6a and an outer device body 6b. The inner device body 6a is arranged in a circular recess 48 of the first ring-shaped mirror 8, whereas the outer device body 6b is formed as a single piece together with the first ring-shaped mirror 8. A radius of the circular recess 48 in a radial direction 90 is large enough to receive the inner device body 6a and the band of optical fibers 10 surrounding a surface 60 of the device body 6. The band of optical fibers 10 is guided through the circular recess 48 of the first ring-shaped mirror 8 along a forward direction 80 on the surface 60 of the device body 6. In this embodiment, the forward directions 80 of all the optical fibers 10 are identical, the forward direction 80 being parallel to a central axis 85 of the device body 6.

A second fiber end 12 of the optical fibers 10 reemerges between the inner device body 6a and the outer device body 6b at a distal end 68 of the device body 6. From there, the second fiber end 12 emits the excitation light 20 towards the first ring-shaped mirror 8, which surrounds the inner device body 6a in a circumferential direction 70. The first ring-shaped mirror 8 reflects the excitation light 20 towards the area 50.

Figure 3:
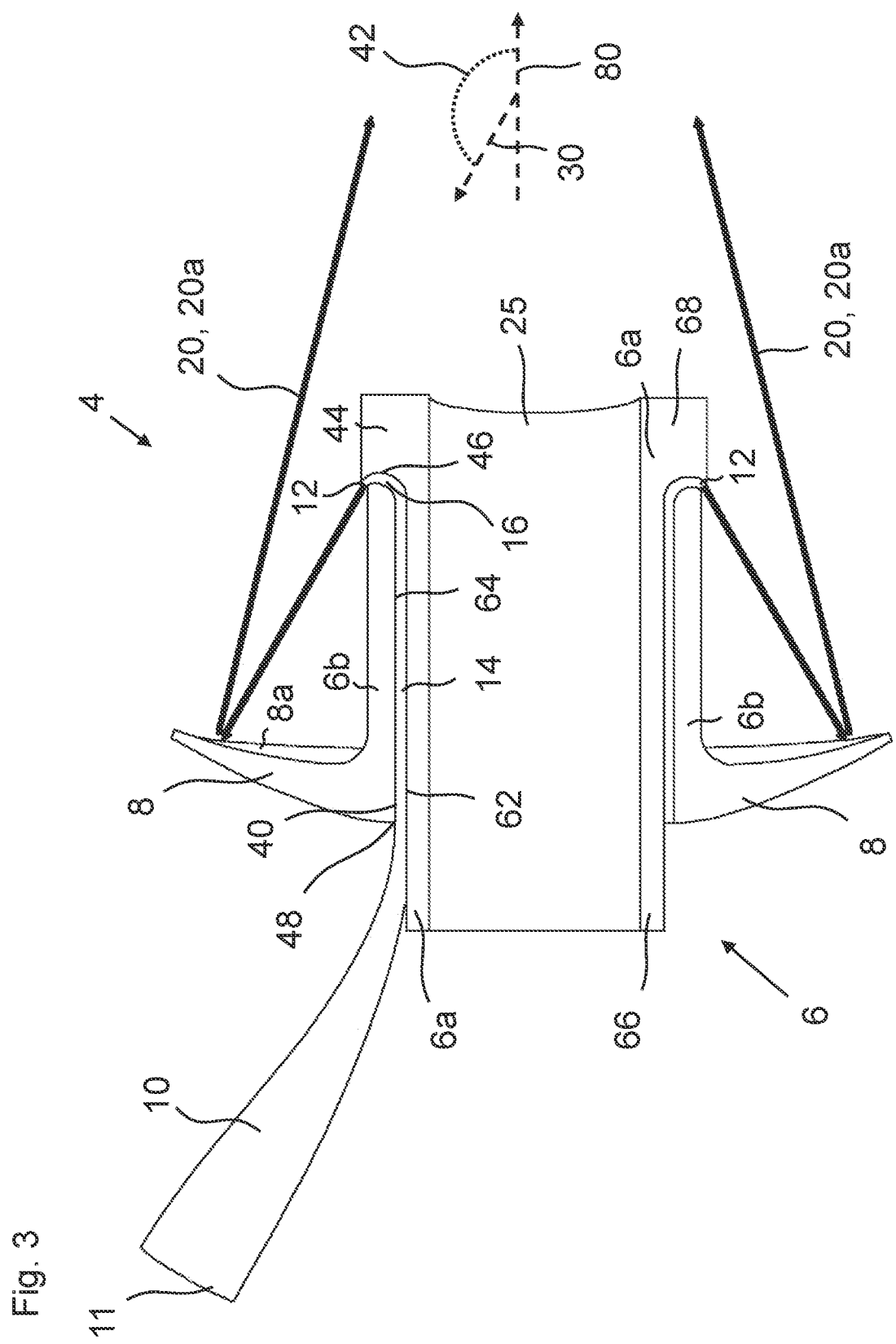
FIG. 3 illustrates a schematic simplified course sectional representation of a first embodiment of a medical lighting device and FIG. 4 illustrates a schematic simplified course sectional representation of a second embodiment of a medical lighting device.

The structure of the medical lighting device 4 shown in FIG. 2 can be easier understood when considering the cross-sectional view shown in FIG. 3. FIG. 3 shows that the diameter of the inner device body 6a is smaller at the proximal end 66 compared to the distal end 68. A segment 14 of the optical fibers 10 is guided through a gap 40 between an outer surface 62 of the inner device body 6a and an inner surface 64 of the outer device body 6b, which in this embodiment forms a single piece with the first ring-shaped mirror 8.

At the distal end 68, the inner device body 6a comprises a sleeve 44 with a curvature 46. An end segment 16 of the optical fibers 10 is bent by the curvature 46 at an angle 42. The bent end segments 16 form a light guiding element. Due to the bending, the second fiber end 12 emits the excitation light 20 in a changed direction 30 towards a reflecting surface 8a of the first ring-shape mirror 8. By fixing the outer device body 6b on the inner device body 6a and/or the optical fibers 10, the optical fibers 10 are held in place. The first ring-shaped mirror 8 reflects the excitation light 20 to the area 50. A focus point of the excitation light 20 is at a point along the central axis 85.

The tubular form of the device body 6 provides an opening 25 on the inside. In this opening 25, the lens unit 24 may be placed to capture the fluorescent light 22. In this way, a compact medical lighting device 4 is realized that is easy to manufacture and can be steam-sterilized.

Figure 4:
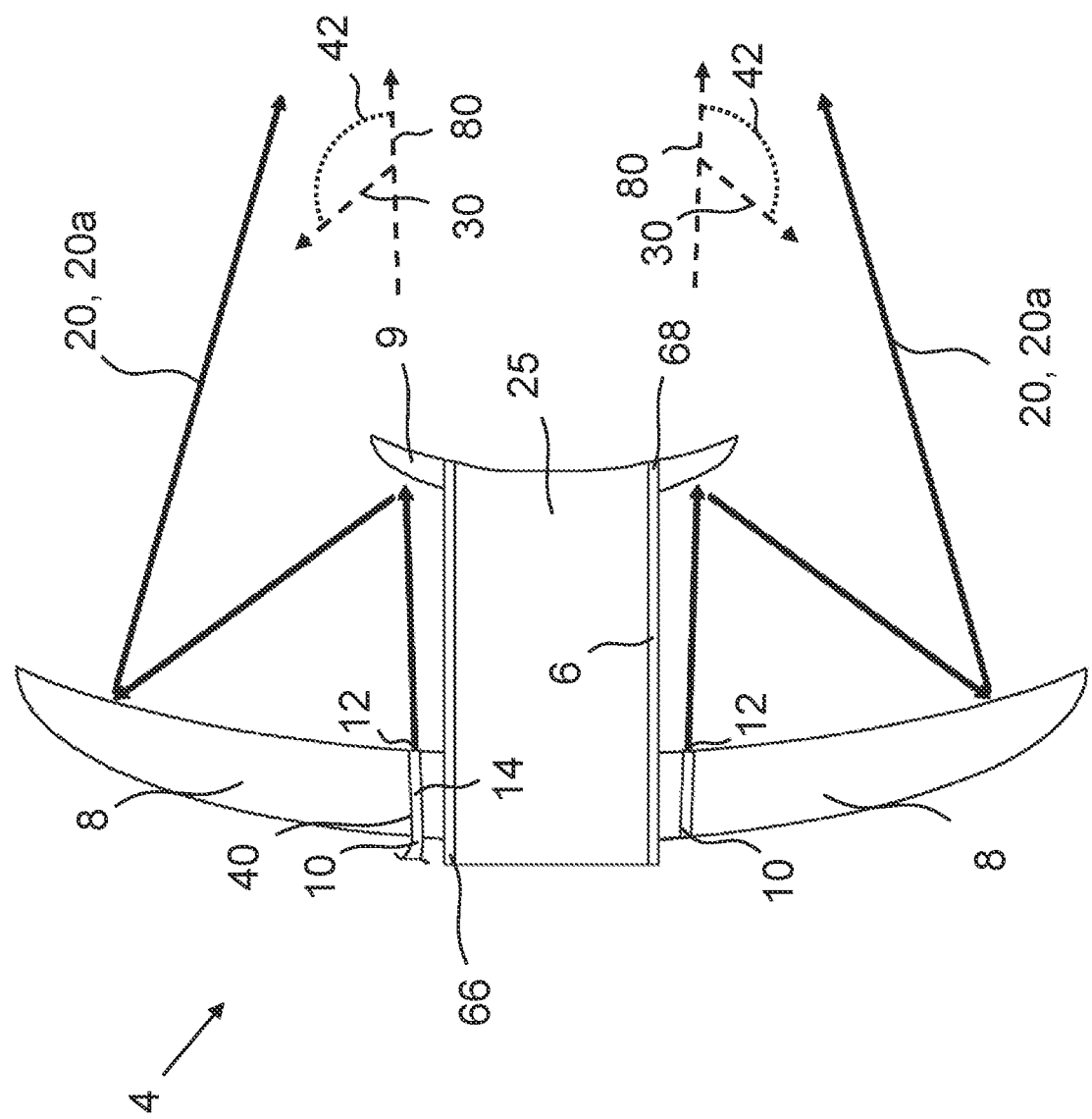

Another embodiment of the medical lighting device 4 is shown in a cross-sectional view in FIG. 4. In this second embodiment, the medical lighting device 4 comprises a second ring-shaped mirror 9 as light guiding element to redirect the excitation light 20 from the forward direction 80 to the changed direction 30. The first ring-shaped mirror 8 is fixed to the device body 6 at a position close to the proximal end 66 and the second ring-shaped mirror 9 is fixed to the device body 6 at a position close to the distal end 68.

In addition, the device body 6 comprises only a single part in the form of a tubular body. Instead of being guided through a gap 40 between the inner device body 6a and the outer device body 6b, the optical fibers pass through a gap 40 in the first ring-shaped mirror 8. The second fiber ends 12 of the optical fibers 10 are positioned at an end of the gap 40, so that the excitation light 20 is emitted in the forward direction 80, before being redirected by the second ring-shaped mirror 9 and reflected by the first ring-shaped mirror 8. In this embodiment, the segments 14 are arranged at a slight angle towards the central axis 85. Thus, the forward directions 80 of the optical fibers 10 are not identical. Still, the excitation light 20 is focused by the first ring-shaped mirror 8 at a single focus point.

Instead, or in addition to guiding the excitation light 20, the medical lighting device 4 may also be applied or used to guide the white light 20a to illuminate the surgical area 50 during surgery. According to one embodiment, the optical fibers 10 guide both, the excitation light 20 and the white light 20a. In other words, a mixture of excitation light 20 and white light 20a are guided in the optical fibers. The white light 20a is visible light, i.e., light visible to the human eye, and has a spectrum comparable to a white light source. This light source can be for example a light bulb, a discharge lamp, a white LED or the like.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES 2 system for fluorescence image guided surgery
4 medical lighting device 5 light guiding optics
6 device body
6a inner device body
6b outer device body
8 first ring-shaped mirror
8a reflecting surface
9 second ring-shaped mirror
10 optical fiber
11 first fiber end
12 second fiber end
14 segment
16 end segment
20 excitation light
20a white light
21, 21a light source
22 fluorescent light
24 lens unit
25 opening
26 image sensor
30 changed direction
40 gap
42 angle
44 sleeve
46 curvature
48 circular recess
50 area
60 surface
62 outer surface
64 inner surface
66 proximal end
68 distal end
70 circumferential direction
80 forward direction
85 central axis
90 radial direction

What is claimed is:

1. A medical lighting device for guiding one or more of excitation light and white light during fluorescence image guided surgery towards a surgical area, the medical lighting device comprising:
a device body; and
light guiding optics;
wherein the device body extends longitudinally in a direction of a central axis from a proximal end to a distal end of the device body, towards an area to be illuminated by the one or more of the excitation light and the white light,
the light guiding optics comprise optical fibers and a first ring-shaped mirror encircling the device body in a circumferential direction of the device body,
the optical fibers each extend from a first fiber end configured to receive the excitation light to a second fiber end configured to emit the one or more of the excitation light and the white light,
a segment of each optical fiber passes through the first ring-shaped mirror while being guided in a forward direction towards the distal end, the ends of the segments are the second fiber ends,
after passing through the first ring-shaped mirror, at least one light guiding element redirects the one or more of the excitation light and the white light from the forward direction to a changed direction back towards the first ring-shaped mirror, and
a reflecting surface of the first ring-shaped mirror is arranged in a path of the one or more of the emitted excitation light and the white light, the first ring-shaped mirror is configured and arranged to reflect the one or more of the emitted excitation light and the white light from the changed direction towards the area to be illuminated by the one or more of the excitation light and the white light.

2. A medical lighting device according to claim 1, wherein an angle between the forward direction and the changed direction is between 90° to 175°.

3. The medical lighting device according to claim 2, wherein the angle is between 120° to 170°.

4. The medical lighting device according to claim 1, wherein:
at least one of the light guiding elements is an end segment of at least one of the optical fibers, and
the end segment is bent from the forward direction to the changed direction so that the second fiber end is positioned to emit the one or more of the excitation light and the white light in the changed direction towards the reflecting surface of the first ring-shaped mirror.

5. The medical lighting device according to claim 4, wherein:
the distal end of the device body comprises a sleeve,
the sleeve comprises a curvature, and
the end segment of the at least one optical fiber is bent by the curvature.

6. The medical lighting device according to claim 1, wherein:
at least one of the light guiding elements is a second ring-shaped mirror,
at least one of the second fiber ends is arranged to emit the one or more of the excitation light and the white light in the forward direction towards the second ring-shaped mirror, and
the second ring-shaped mirror is configured and arranged to reflect the one or more of the excitation light and the white light in the changed direction towards the reflecting surface of the first ring-shaped mirror.

7. The medical lighting device according to claim 1, wherein:
the device body comprises an inner device body and an outer device body,
the outer device body surrounds the inner device body in the circumferential direction, and
the first ring-shaped mirror surrounds the outer device body in the circumferential direction.

8. The medical lighting device according to claim 7, wherein the segments pass through the first ring-shaped mirror by passing through a gap between an inner surface of the outer device body and an outer surface of the inner device body.

9. The medical lighting device according to claim 7, wherein the outer device body is fixed on one or more of the inner device body and the optical fibers to hold the optical fibers in place.

10. The medical lighting device according to claim 1, wherein the first ring-shaped mirror is a concave mirror.

11. The medical lighting device according to claim 6, wherein the second ring-shaped mirror is a convex mirror.

12. The medical lighting device according to claim 1, wherein the first ring-shaped mirror is shaped as a parabolic or spherical reflector with a circular recess in its middle, and the device body is arranged in the circular recess.

13. The medical lighting device according to claim 1, wherein the first ring-shaped mirror is movable parallel to the central axis of the device body in relation to the light guiding element.

14. The medical lighting device according to claim 13, wherein the first ring-shaped mirror is movable parallel to the central axis of the device body in relation to the light guiding element, and in relation to the inner device body.

15. The medical lighting device according to claim 1, wherein the device body has a tubular form with an opening.

16. The medical lighting device according to claim 15, wherein the opening extending along the central axis.

17. The medical lighting device according to claim 16, wherein the segments of the optical fibers run outside a surface area of the device body.

18. A system for fluorescence image guided surgery, the system comprising:
    the medical lighting device according to claim 1,
    a light source to provide the one or more of the excitation light and the white light for the medical lighting device,
    a lens unit to capture fluorescence light from the surgical area; and
    an image sensor arranged to receive the fluorescence light from the lens unit.

19. A method for manufacturing the medical lighting device according to claim 1, wherein the segments of the optical fibers are arranged at different circumferential positions of the device body, each segment extending along the forward direction.

20. The method according to claim 19, further comprising one or more of gluing together, smoothing and polishing the optical fibers after being arranged at the different circumferential positions.

21. The method according to claim 19, further comprising:
    placing the segments of the optical fibers in a position on the outer surface of the inner device body, and
    fixing the segments in the position by placing and fixing the outer device body on the inner device body, thereby enclosing the segments in a gap between the inner device body and the outer device body.

* * * * *